(12) United States Patent
Dahlgren et al.

(10) Patent No.: US 6,453,725 B1
(45) Date of Patent: Sep. 24, 2002

(54) GAS CHROMATOGRAPH SAMPLE AND COLUMN-SWITCHING VALVE

(75) Inventors: Robert W. Dahlgren; Robert K. Bade; Stephen B. Hunt, all of Bartlesville, OK (US)

(73) Assignee: Siemens Energy & Automation, Alpharetta, GA (US)

( * ) Notice: Subject to any disclaimer, the term of this patent is extended or adjusted under 35 U.S.C. 154(b) by 0 days.

(21) Appl. No.: 09/226,735

(22) Filed: Jan. 7, 1999

(51) Int. Cl.⁷ .............................. G01N 30/04; F16K 7/00
(52) U.S. Cl. ...................... 73/23.42; 137/863; 137/869; 137/885; 251/61.1; 251/62
(58) Field of Search .............................. 73/23.42, 23.35, 73/23.37, 863.72, 863.73; 137/863, 869, 596.18, 885, 600, 602; 251/61.1, 62

(56) References Cited

U.S. PATENT DOCUMENTS

| | | | |
|---|---|---|---|
| 3,140,615 A | * 7/1964 | Broerman | 73/863.71 |
| 3,492,873 A | * 2/1970 | Broerman | 251/62 |
| 3,770,012 A | * 11/1973 | Bitzer et al. | 137/596.16 |
| 4,186,607 A | * 2/1980 | Porter et al. | 73/61.55 |
| 4,353,243 A | * 10/1982 | Martin | 73/23.43 |
| 4,553,985 A | * 11/1985 | Dahlgren et al. | 73/23.39 |
| 4,848,722 A | * 7/1989 | Webster | 251/61.1 |
| 4,869,282 A | * 9/1989 | Sittler et al. | 137/15.01 |
| 5,083,742 A | * 1/1992 | Wylie et al. | 251/61.1 |
| 5,095,931 A | * 3/1992 | Kawabe | 137/1 |

* cited by examiner

Primary Examiner—Hezron Williams
Assistant Examiner—Michael Cygan (57) ABSTRACT

A multiport, diaphragm sealed valve suitable for use as both a sampling and column switching valve. The valve is constructed to internally block fluid communication between one or more pairs of ports in a valve operating mode. Such blocking may be used to conserve carrier gas when the valve is in the ON position.

24 Claims, 9 Drawing Sheets

SECTION A-A

GAS CHROMATOGRAPH SAMPLE AND COLUMN-SWITCHING VALVE

FIELD OF THE INVENTION

This invention relates to valves used in gas chromatographs ("GC") and more particularly to such a valve that internally blocks fluid communication between ports.

DESCRIPTION OF THE PRIOR ART

All process GCs include a sample valve. The function of such a valve is to collect a precise volume of a liquid or vapor sample. The components of the collected sample are then separated by the one or more columns in the GC based on some physical or chemical property. The one or more detectors inside the GC are used to sense the separated components as they leave the end of the one or more columns so that component concentrations can be determined.

Figure 1:
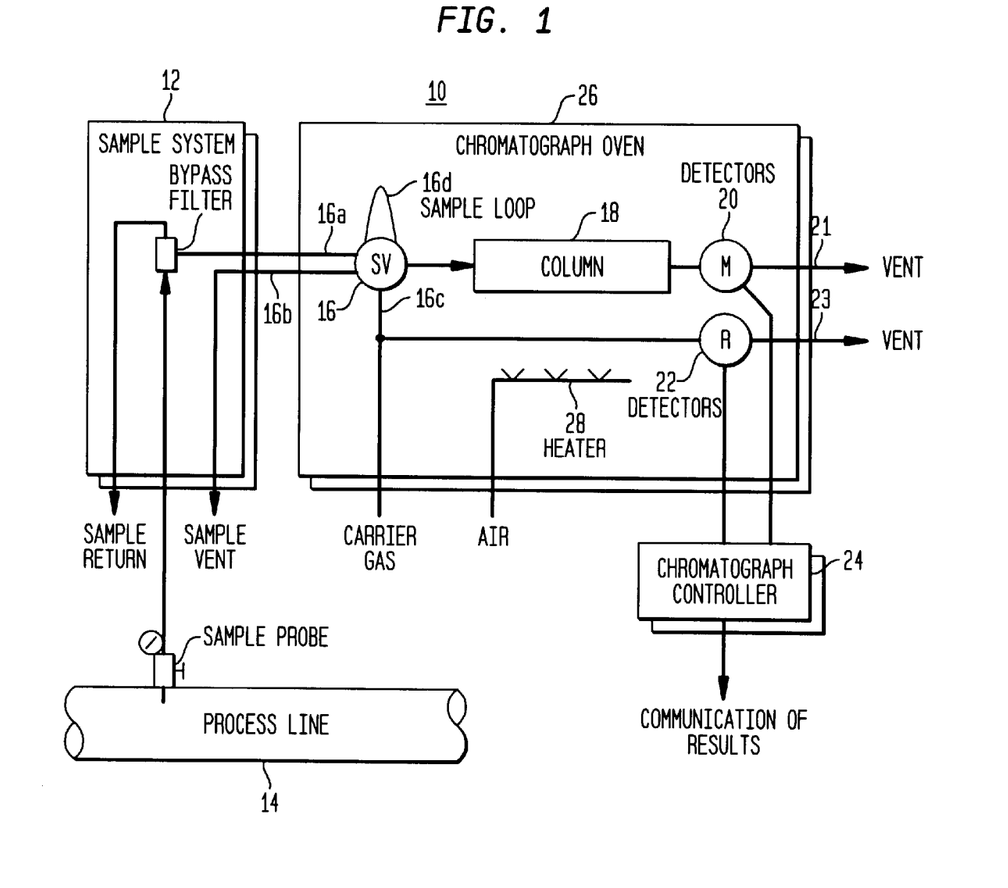
FIG. 1 shows a simplified block of an on-line gas chromatograph.

Referring to FIG. 1 there is shown a simplified block diagram of an on-line process GC 10. GC 10 has a sample extraction and conditioning system 12 which is used to remove a sample from process stream 14. The sample is conditioned to filter contaminants out of the sample before it enters sample valve 16 through sample input port 16a. The valve 16 has also has a sample output port 16b for returning the sample to the sampling and conditioning system 12 and a port 16c for injection of carrier gas. A fixed volume of the sample mixture is injected into the flowing carrier gas stream through port 16a to start the analysis cycle. The function of sample valve 16 is to trap a constant volume of sample in a sample loop 16d and periodically inject the sample into the flowing carrier gas.

The chromatograph column 18 includes a packing, not shown, which may be either a fixed bed of tiny liquid coated particles, tiny porous particles, or the coating on the wall of a capillary tube. The packing is known as the stationary phase and its function is to separate the chemicals in the sample based on some physical or chemical property. The carrier gas sweeps or carries the sample through or past the stationary phase.

GC 10 includes a measuring detector 20 which is located at the outlet of column 18 and produces a signal proportional to the concentration of each component band passing through the detector. GC 10 also includes a reference detector 22 which is exposed to pure carrier gas. Detectors 20 and 22 are connected to vents 21 and 23, respectively. The electrical signals from detectors 20 and 22 are connected to chromatograph controller 24. Controller 24 amplifies, digitizes and integrates the raw electrical signal from detector 20 and produces an output signal when detector 20 is exposed to components leaving the end of column 18 while the reference detector 22 is exposed to nothing but pure carrier gas.

As can be seen from FIG. 1, sample valve 16, column 18, and detectors 20 and 22 are contained in the oven 26 of GC 10. Oven 26 includes a heater 28. The oven ensures that high boiling point liquid samples are vaporized in the sampling valve 16 and also keeps components from condensing.

In addition to being used as sample valves, chromatograph valves are also used as column switching valves. A column switching valve is used to redirect the carrier gas flow during an analysis cycle to load specific components onto different columns for further separation. Column switching valves are also used to reverse the flow of carrier gas through a column and backflush components not of interest off the column to a vent.

Prior art sample and column switching valves usually includes a multiplicity of ports but do not provide internal blocking of fluid communication between one or more pairs of ports. Two examples of such valves are the four port double diaphragm model 44 valve and six port double diaphragm model 46 valve both of which are sold by Applied Automation, Inc. of Bartlesville, Okla. It is desirable to preserve the full functionality of all of the ports in the valve. It is also desirable in a GC to conserve carrier gas.

In many applications where a prior art valve is used, carrier gas should not flow out of a particular port or ports when the valve is in one of its two operating modes but should flow out of that port or ports when the valve is in the other of its operating modes. Blocking the port or ports would not accomplish that result as the port or ports are then blocked for both operating modes. Therefore, prior art valves have included additional hardware external to the valve to regulate the flow out of that port or ports. Such regulated flow is however a waste of carrier gas in that valve operating mode where carrier gas should not flow out of the port or ports.

As was described above, the sample valve along with the column and the detectors are inside of the oven in the GC. The GC oven is of a predetermined size and if external hardware is added to the sample valve to regulate the flow out of a port or ports that external hardware must also reside in the oven. Therefore, the addition of external hardware to the sample valve reduces the room in the oven for additional columns and detectors.

SUMMARY OF THE INVENTION

A valve having at least four ports. The valve has first and second operating modes. When the valve is in the first operating mode the at least four ports become at least two pairs of adjacent ports in fluid communication with each other internal to the valve and at least two pairs of adjacent ports not in fluid communication with each other internal to the valve. At least one pair of the at least two adjacent port pairs not in fluid communication with each other internal to the valve when the valve is in the first operating mode separate at least one pair of the at least two port pairs that are in fluid communication with each other internal to valve when the valve is in the first operating mode.

The valve has a first plate which has on its periphery the at least four ports for entry and exit of a first fluid. The at least four ports are in fluid communication with at least four openings in each of the first and second exterior surfaces of the first plate. Each of the at least four openings are associated with a respective one of the at least four ports. The at least four openings in the first exterior surface are blocked when the valve is in the second operating mode.

The valve also has a second plate which has a valve for entry of a second fluid. The second plate also has a first exterior surface which has at least one opening which is in fluid communication with the second plate second fluid entry valve. The valve further has a first diaphragm between the second exterior surface of the first plate and the first exterior surface of the second plate. The first diaphragm pressing against the second plate first exterior surface when the valve is in the second operating mode.

The at least one opening in the first exterior surface of the second plate allows, when the valve is in the second operating mode, fluid communication internal to the valve between all but at least one of the at least two port pairs not in fluid communication with each other internal to the valve when the valve is in the first operating mode.

A process gas chromatograph which has a valve having at least four ports which is embodied as described above, at least one separation column connected to a port of the at least four port valve, and at least one detector connected to the at least one separation column.

A valve having at least 2N ports, where N≧2. The valve also has first and second operating modes. When the valve is in the first operating mode the at least 2N ports become at least N pairs of adjacent ports in fluid communication with each other internal to the valve and at least N pairs of adjacent ports not in fluid communication with each other internal to the valve. At least one pair of the at least N adjacent port pairs not in fluid communication with each other internal to the valve when the valve is in the first operating mode separate at least one pair of the at least N port pairs that are in fluid communication with each other internal to valve when the valve is in the first operating mode.

The valve has a first plate which has on its periphery the at least 2N ports for entry and exit of a first fluid. The at least 2N ports are in fluid communication with at least 2N openings in each of first and second exterior surfaces of the first plate. Each of the at least 2N openings are associated with a respective one of the at least 2N ports. the at least 2N openings in the first exterior surface are blocked when the valve is in the second operating mode.

The valve also has a second plate which has a valve for entry of a second fluid and a first exterior surface having at least N−1 openings each of which are in fluid communication with the second plate second fluid entry valve. The valve further has a first diaphragm between the second exterior surface of the first plate and the first exterior surface of the second plate. The first diaphragm presses against the second plate first exterior surface when the valve is in the second operating mode. the at least N−1 openings in the first exterior surface of the second plate allowing when the valve is in the second operating mode fluid communication internal to the valve between all but at least one of the at least N port pairs not in fluid communication with each other internal to the valve when the valve is in the first operating mode.

A process gas chromatograph which has a multi port valve which is embodied as described above, at least one separation column connected to a port of the multiport valve, and at least one detector connected to the at least one separation column.

DESCRIPTION OF THE PREFERRED EMBODIMENT(S)

Figure 2:
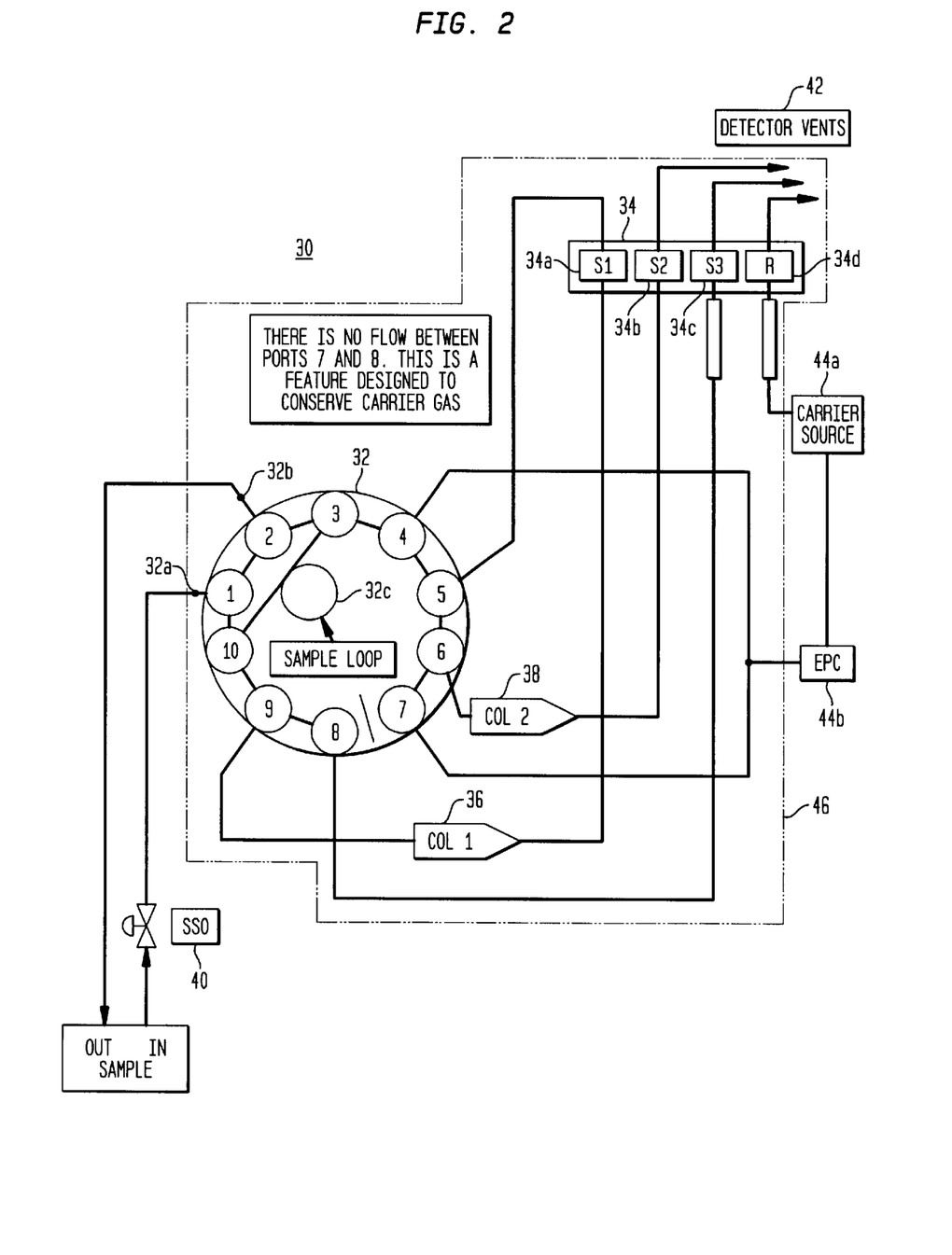
FIG. 2 shows a schematic diagram of a gas chromatograph that includes the valve of the present invention.

Referring now to FIG. 2, there is shown a schematic diagram for using the valve 32 of the present invention in a GC 30 that has a multi-cell detector 34. GC 30 also has first and second columns 36 and 38, sample shutoff valve (SSO) 40, detector vents 42, a carrier source 44a, an electronic pressure control (EPC) 44b which is used to bring the carrier gas into the GC and an oven 46 which is shown in FIG. 2 by the dashed box. The heater typically included in oven 46 has been omitted from FIG. 2 for ease of illustration. The valve 32, multi-cell detector 34, and first and second columns 36 and 38 are in the oven 46.

Multi-cell detector 34 includes a first sensor (S1) 34a, a second sensor (S2) 34b, and a third sensor (S3) 34c and a reference (R) 34d.

Figure 3A:
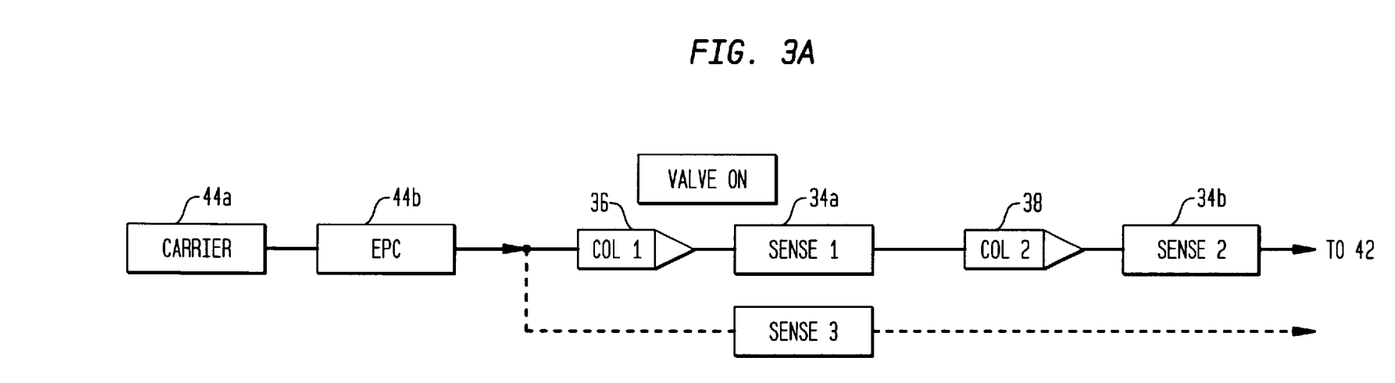
FIG. 3a shows simplified flow diagram showing carrier gas flow when the valve of FIG. 2 is in the ON position.

Referring now to FIG. 3a, this figure illustrates a simplified flow diagram showing how the carrier gas flows through valve 32, columns 36 and 38 and multi-cell detector 34 to detector vents 42 when the valve 32 is in the ON position. As can be seen from FIG. 3a, when valve 32 is ON, carrier gas flows through first column 36, first sensor 34a, the second column 38 and finally through the second sensor 34b to the detector vents 42.

Figure 3B:
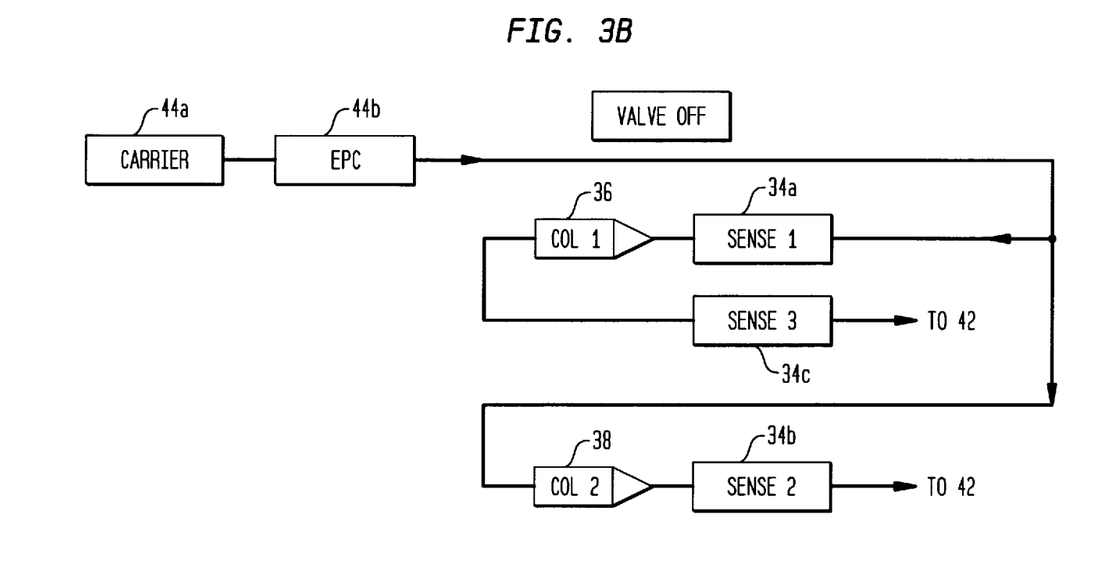
FIG. 3b shows simplified flow diagram showing carrier gas flow when the valve of FIG. 2 is in the OFF position.

Referring now to FIG. 3b, this figure illustrates a simplified flow diagram showing how the carrier gas flows through the valve 32, columns 36 and 38 and multi-cell detector 34 to detector vents 42 when the valve 32 is in the OFF position. As can be seen from FIG. 3b, when valve 32 is OFF, carrier gas flows into both first sensor 34a and the second column 38. The carrier gas that flows through the first sensor 34a then flows through the first column 36 and finally through the third sensor 34c to the detector vents 42. The carrier gas that flows through the second column 38 then flows through the second sensor 34b to the detector vents 42.

Valve 32 has ten ports which are shown symbolically in FIG. 2 by the ten circles numbered 1–10 on the top surface of valve 32. In FIG. 2, the solid lines in the top surface of valve 32 illustrate the flow of fluid through valve 32 when the valve is in the OFF position and the dashed lines illustrate the flow of fluid through the valve when the valve is in the ON position. The flow of sample through valve 32 and the flow of carrier gas described in connection with FIG. 3a and 3b for the valve in the ON and OFF positions will now be described again but with reference to the ten ports shown in FIG. 2.

When the valve 32 is in the OFF position, port 1 is in fluid communication with port 10, port 2 is in fluid communication with port 3 and a sample loop 32c extends between ports 10 and 3. Port 1 is connected to the sample input 32a of the valve and port 2 is connected to the sample output 32b of the valve. Therefore, a sample to be analyzed flows from port 1 to port 10 and then through the sample loop 32c to port 3. From port 3 the sample flows to port 2 and thus out of valve 32.

After the sample loop 32c has been filled, valve 32 is actuated to the ON position. In that position, port 1 is in fluid communication with port 2; port 3 is in fluid communication with port 4; port 5 is in fluid communication with port 6; and port 9 is in fluid communication with port 10. Sample enters the valve through port 1 and immediately exits the valve through port 2. Carrier gas enters the valve through port 4.

The carrier gas flows from port 4 to port 3 and into the sample loop 32c forcing the sample in the loop to flow from port 10 to port 9. The sample then flows out of port 9, through first column 36 and first detector 34a to port 5. Since port 5 is in fluid communication with port 6, the sample flows out of port 6 and through the second column 38 and second detector 34b to the detector vents 42.

Carrier gas also enters the valve 32 through port 7 when the valve is in the ON position. In order for the carrier gas to flow through the third detector 34c as is shown by the dashed path in FIG. 3a, the carrier gas must flow out of port 8. As can be seen from FIG. 2, there is no fluid communication in valve 32 between ports 7 and 8 and thus carrier gas does not flow through the third detector 34c when the valve 32 is in the ON position.

Returning again to the OFF position of valve 32, port 4 is in fluid communication with port 5; port 6 is in fluid communication with port 7; and port 8 is in fluid communication with port 9. Carrier gas enters valve 32 by flowing through port 4. The carrier gas then flows out of the valve through port 5 and through the first sensor 34a and the first column 36 to port 9. The direction of carrier gas flow through the first sensor 34a and the first column 36 is in a direction opposite to the flow through that sensor and column when the valve is in the ON position. The carrier gas then reenters the valve 32 by flowing through port 9 and exits the valve by flowing through port 8 which is in fluid communication with the third sensor 34c. The carrier gas thus flows through the third sensor 34c to the detector vents 42. The reverse flow of carrier gas through the first column 36 provides all of the sample components in that column to the third sensor 34c so that sensor can provide a composite peak reading of the sample.

When valve 32 is in the OFF position, carrier gas also enters the valve by flowing through port 7 and exits the valve by flowing through port 6 which is in fluid communication with the second column 38. The carrier gas then flows through the second column 38 and the second sensor 34b to provide a reading of the peak components in the sample and then to the detector vents 42.

As was described above, there is no fluid communication in valve 32 between ports 7 and 8 when the valve is in the ON position. This blocking of fluid communication between ports 7 and 8 when valve 32 is in the ON position is accomplished in accordance with the present invention internal to valve 32 in a manner which will be described below. Externally blocking port 8 would not provide the same result as that port must not be blocked, as is shown by the upper flow path of FIG. 3b, when valve 32 is in the OFF position. Therefore, the valve of the present invention using internal blocking of a port allows carrier gas to be conserved when the valve is in the ON position and the third sensor 34c to provide a composite peak reading when the valve is in the OFF position.

Figure 4:
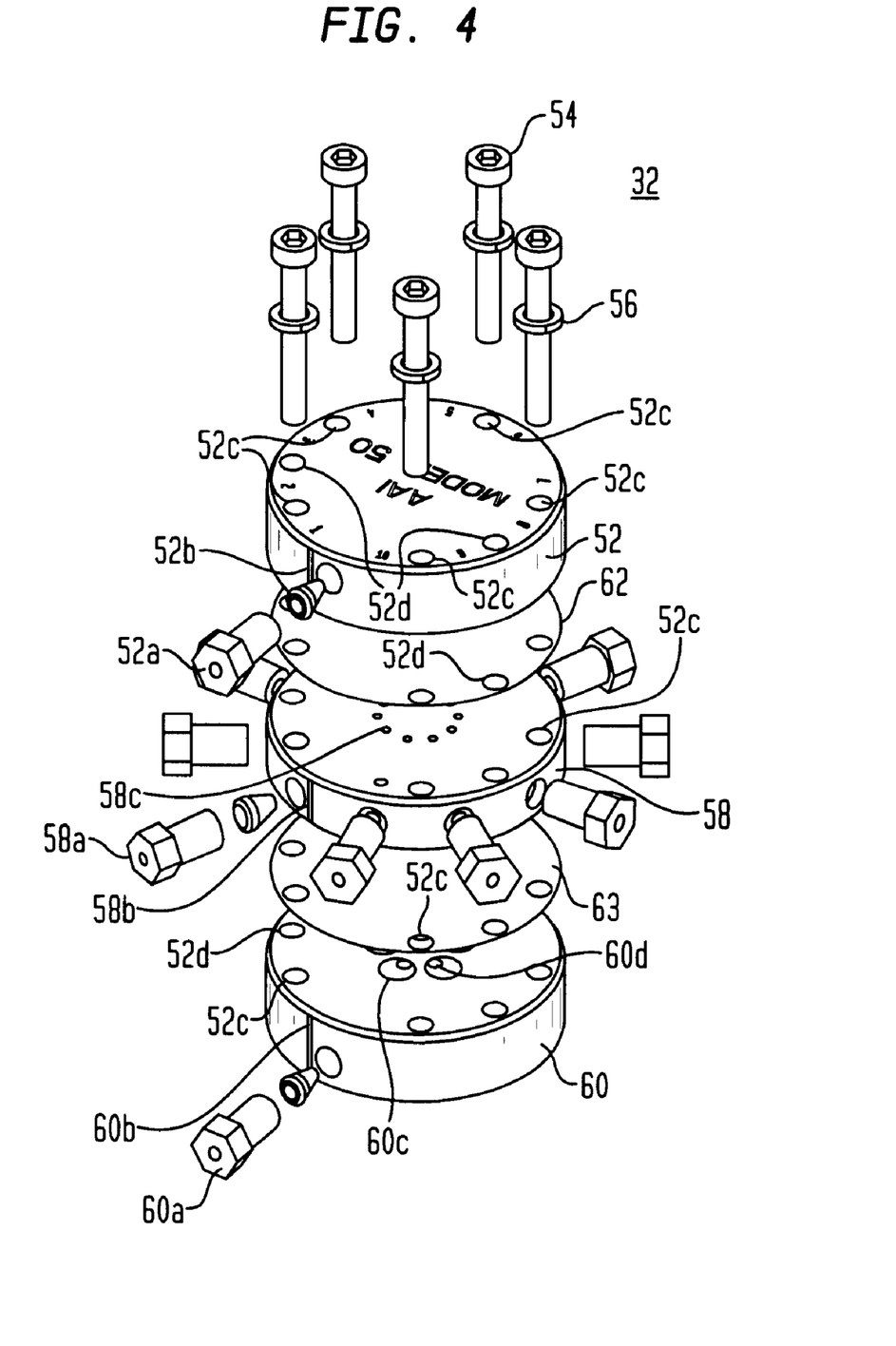
FIG. 4 shows an exploded perspective of the valve of the present invention.

Referring now to FIG. 4, there is shown an exploded perspective for valve 32 of the present invention. Valve 32 has a cylindrical top plate 52 that has on the top surface thereof the numbers 1–10 which designate an associated one of the ten ports in the valve. The bottom surface of top plate 52, which is not visible in FIG. 4 but is shown in FIG. 5c, has five circular openings 52e near the center thereof. As can be seen in FIG. 5c, each of the centrally located circular openings 52e has a smaller circular opening 52f.

Top plate 52 has on its periphery an index line 52b which is used to align the top plate with the other plates of valve 32 when the valve is assembled. The index line 52b also identifies the location of the first port. Top plate 52 also has five holes 52c which extend the entire length of valve 32. The holes 52c are used to receive screws 54 when the valve is assembled. Each screw has a spring lock washer 56 mounted thereon. The top plate also has two additional holes 52d which also extend the entire length of the valve and can be used to mount the valve to a bracket.

Valve 32 also has cylindrical middle plate 58, cylindrical bottom plate 60 and diaphragms 62, 63. Diaphragm 62 is between top plate 52 and middle plate 58 and diaphragm 63 is between middle plate 58 and bottom plate 60. The middle and bottom plates 58, 60 and diaphragms 62, 63 also each have the five holes 52c to receive screws 54 and the two holes 52d to mount the valve to a bracket.

Top plate 52 also has on its periphery a fitting 52a which is an input for an actuation gas that is used to cause diaphragm 62 to move downwardly and press against the top surface of middle plate 58 when the valve 32 is actuated to the ON position. The actuation gas flows out of the top plate through the five small circular openings 52f (see FIG. 5c). The actuation gas may be any non-corrosive gas such as air, nitrogen or helium. Bottom plate 60 has on its periphery a fitting 60a which is an input for the actuation gas to cause diaphragm 63 to move upwardly and press against the bottom surface of middle plate 58 when the valve 32 is actuated to the OFF position.

Figures 6A, 6B:
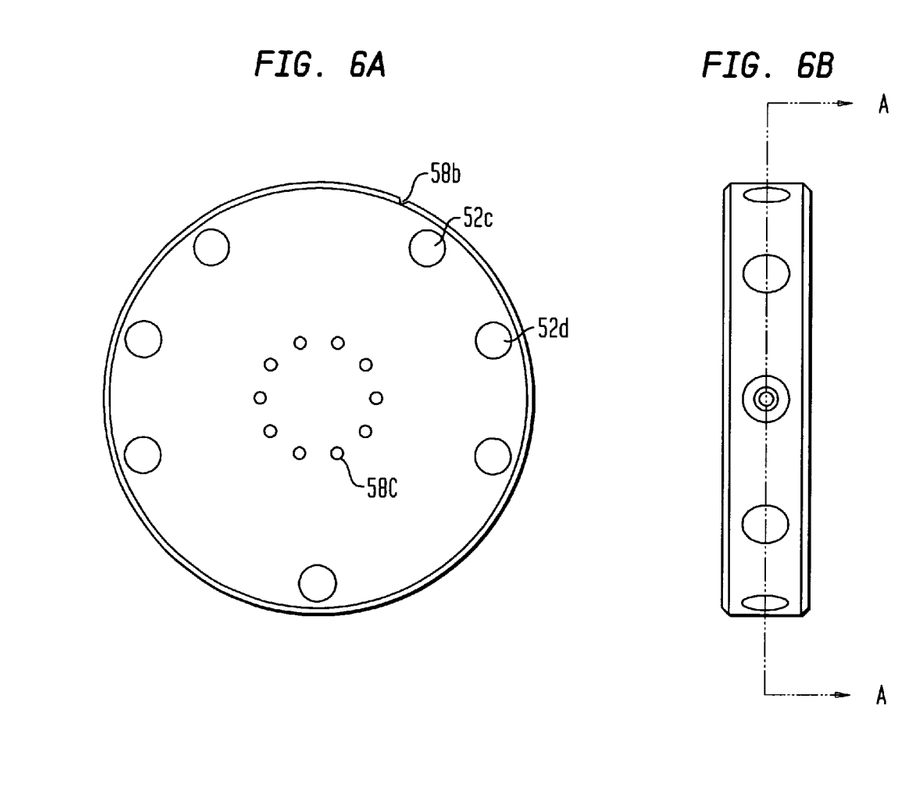
FIGS. 6a, 6b and 6c show, respectively, top, side and cross sectional views of the middle plate of the valve.
Figure 6C:
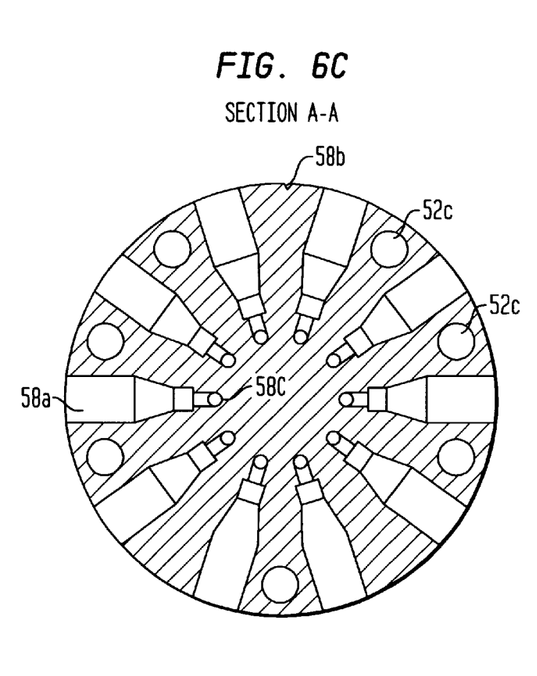

Middle plate 58 has ten fittings 58a (only eight of which are shown in FIG. 4) around its periphery and an index line 58b. Each of the ten fittings 58a is associated with a respective one of ports 1–10. Middle plate also has on its top surface close to the center thereof ten circular openings 58c which extend through the entirety of the middle plate to the bottom surface thereof. While only eight of the circular openings are shown in FIG. 4, all ten of the openings are shown in FIG. 6a. As is shown in FIG. 6c, each of the openings 58c is associated with a respective one of ports 1–10. Therefore carrier gas and sample that enters the valve through one of ports 1–10 can flow both upwardly to the top surface of middle plate 58 and downwardly to the bottom surface of that plate.

Bottom plate 60 also has on its periphery an index line 60b. The top surface of bottom plate 60 has four circular openings 60c near the center thereof each of which has a smaller circular opening 60d. The actuation gas flows out of bottom plate through the openings 60d. All four of the openings 60c and 60d are shown in FIG. 7a.

Figure 5A:
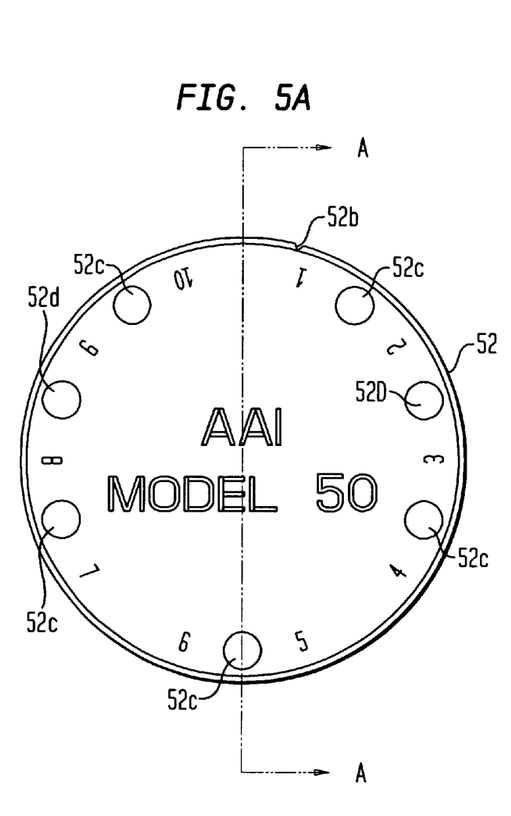
FIGS. 5a, 5b and 5c show, respectively, top, cross sectional and bottom views of the top plate of the valve.
Figure 5B:
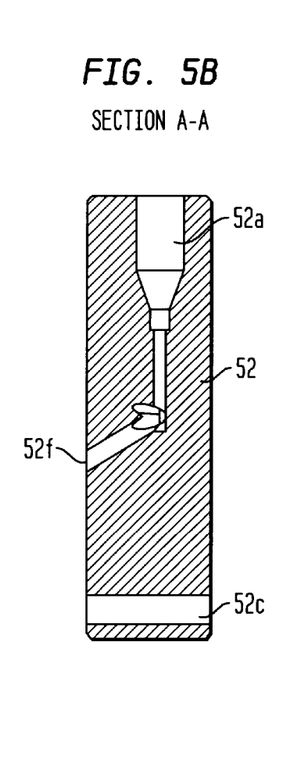
Figure 5C:
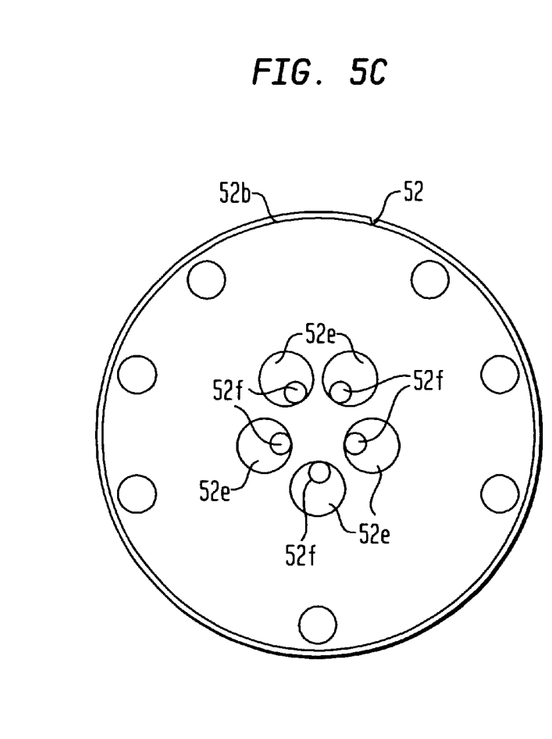

Referring now to FIGS. 5a, 5b and 5c there is shown respectively a top, cross section and bottom view of top plate 52. FIG. 5b shows one of the holes 52c for receiving screws 54 and the passage for the flow of actuation gas fitting 52a to circular opening 52f. The five centrally located openings 52e each of which have the smaller circular opening 52f in the bottom surface of top plate 52 are shown in FIG. 5c.

Referring now to FIGS. 6a, 6b and 6c there is shown respectively a top, side and sectional view of middle plate 58. As can be seen from FIG. 6c, each of the ten ports communicate with an associated one of the openings 58c to thereby allow carrier gas and sample to flow from a port to both the top and bottom surfaces of the middle plate. The opening 58c also allows carrier gas and sample to flow from one of those surfaces to a port depending on which of the two diaphragms 62, 63 is pressing against the associated surface of the middle plate.

Figure 7A:
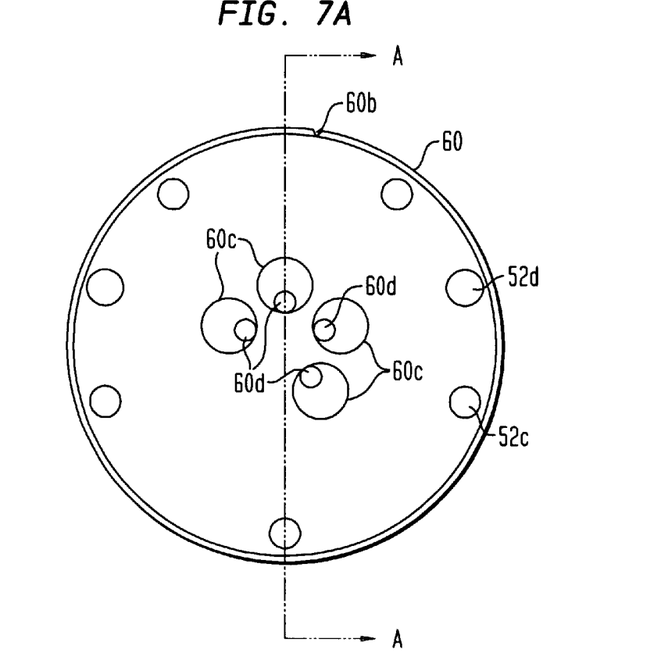
FIGS. 7a and 7b show, respectively, top and cross sectional views of the lower plate of the valve.
Figure 7B:
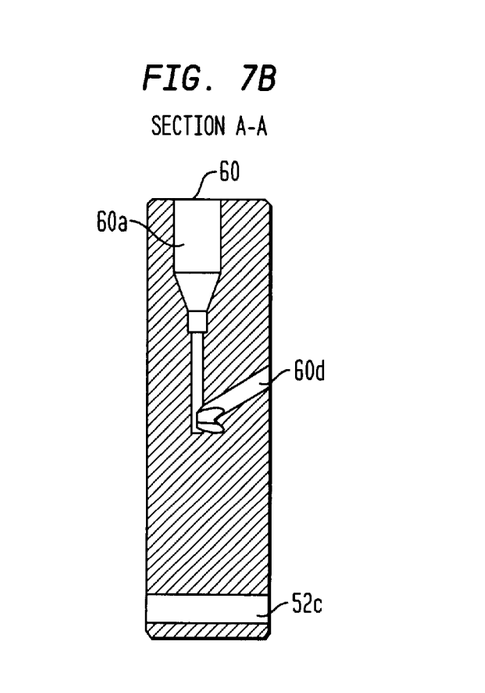

Referring now to FIGS. 7a and 7b there is shown respectively a top view of bottom plate 60 and a sectional view through the plate 60. As is shown in FIG. 7a, the top surface of bottom plate 60 has four centrally located openings 60c each of which have a smaller circular opening 60d. FIG. 7b shows one of the holes 52c for receiving screws 54 and the passage associated with hole 60d for the flow of actuation gas.

Figure 8A:
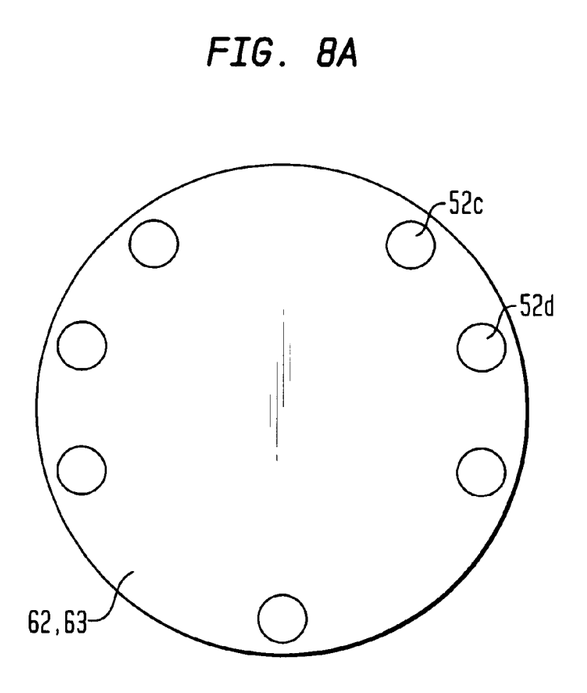
FIGS. 8a and 8b show, respectively, top or bottom, and side views of either of the two diaphragms in the valve.
Figure 8B:
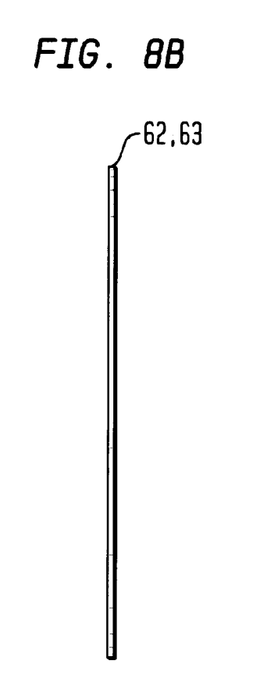

Referring now to FIGS. 8a and 8b there is shown respectively a top or bottom view of diaphragm 62, 63 and a side view of diaphragm 62, 63.

Figure 9:
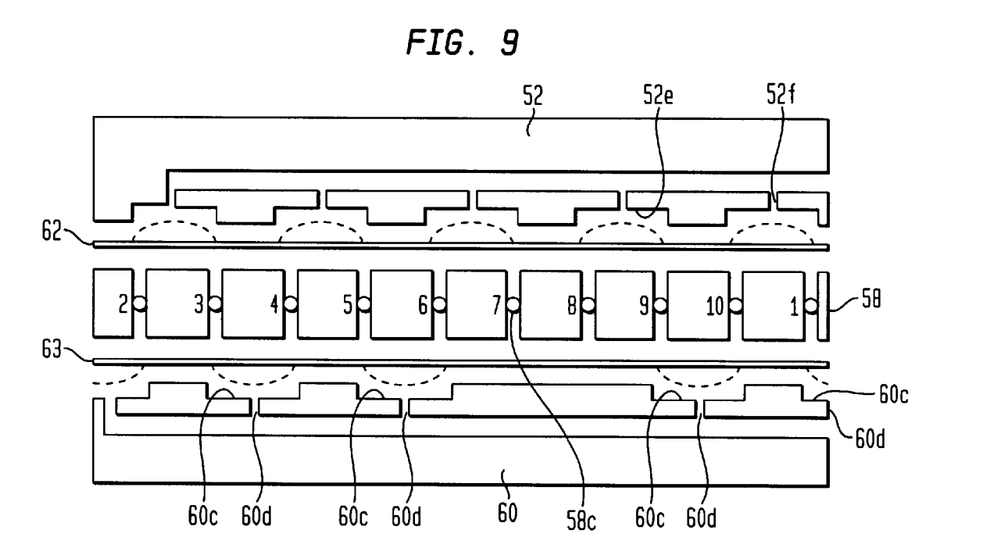
FIG. 9 shows a view of the top, middle and bottom plates and diaphragms of the valve as if these elements are linear elements.

As is shown in FIG. 4, valve 32 is cylindrical in shape. A better understanding of the operation of valve 32 can be obtained if the top, middle and bottom plates 52, 58 and 60 and diaphragms 62 and 63 are shown as linear elements. Such a view of valve 32 is shown in FIG. 9.

When actuation gas is applied to the top plate 52 through fitting 52a (see FIG. 4) the valve is actuated to the ON position. The actuation gas causes the diaphragm 62 to press against the top surface of middle plate 58 to thereby block the flow of sample and carrier gas out of the holes 58c in that surface. Therefore, carrier gas and sample that enters the middle plate 58 through a port can only flow out of the bottom surface of the plate towards the top surface of diaphragm 63. Since diaphragm 63 does not have actuation gas applied to it that diaphragm can be displaced downwardly toward the top surface of bottom plate 60.

Carrier gas and sample that enter the center plate 58 through one of the ports 1–10 flows to an adjacent port by displacing the diaphragm 63 into the four reliefs in the top surface of bottom plate 60. The reliefs are the four centrally located circular openings 60c (see FIG. 7a) in the top surface of bottom plate 60. The smaller circular opening 60d in each relief allows actuation gas to flow from fitting 60a to the bottom surface of diaphragm 63 and thereby cause that diaphragm to press against the bottom surface of middle plate 58 to actuate the valve to the OFF position.

When valve 32 is assembled the four openings 60c are aligned with the holes 58c such that when the valve is in the ON position the flowing carrier gas and sample causes diaphragm 63 to move downwardly to allow flow between four pair of ports, namely, ports 1 and 2, ports 3 and 4, ports 5 and 6, and ports 9 and 10. This flow is indicated in FIG. 9 by the dashed lines on the bottom surface of diaphragm 63.

As was discussed in connection with FIG. 2, fluid communication between ports 7 and 8 is blocked internally to the valve 32 when the valve is in the ON position. This internal blocking of fluid communication between these two ports is accomplished in the manner described below. Since the top surface of bottom plate 60 only has four circular openings there is not as is shown in FIG. 9 a circular opening 60c adjacent ports 7 and 8 when valve 32 is assembled. Therefore, as can be seen from FIG. 9, there isn't any relief in the top surface of bottom plate 60 between ports 7 and 8. Thus in response to the flow of carrier gas and sample when valve 32 is in the ON position diaphragm 63 cannot move downwardly in the vicinity of ports 7 and 8 to thereby allow flow between those two ports and as such flow is blocked between those ports when the valve is in the ON position.

When actuation gas is applied to the bottom plate 60 through fitting 60a (see FIG. 4) the valve is actuated to the OFF position. The actuation gas causes the diaphragm 63 to press against the bottom surface of middle plate 58 to thereby block the flow of sample and carrier gas out of the holes 58c in that surface. Therefore, carrier gas and sample that enters the middle plate 58 through a port can only flow out of the top surface of the middle plate 58 towards the bottom surface of diaphragm 52. Since diaphragm 62 does not have actuation gas applied to it that diaphragm can be displaced upwardly toward the bottom surface of top plate 60.

Carrier gas and sample that enter the center plate 58 through one of the ports 1–10 flows to an adjacent port by displacing the diaphragm 62 into the reliefs in the bottom surface of top plate 52. The reliefs are the five centrally located circular openings 52e (see FIG. 5c) in the bottom surface of top plate 52. The smaller circular opening 52f in each relief allows actuation gas to flow from fitting 58a to the top surface of diaphragm 62 and thereby cause that diaphragm to press against the top surface of middle plate 58 to actuate the valve to the ON position.

When valve 32 is assembled the five openings 52e are aligned with the holes 58c such that when the valve is in the OFF position the flowing carrier gas and sample causes diaphragm 62 to move upwardly to allow flow between five pair of ports, namely, ports 1 and 10, ports 2 and 3, ports 4 and 5, ports 6 and 7, and ports 8 and 9. This flow is indicated in FIG. 9 by the dashed lines on the top surface of diaphragm 62.

The present invention has been described in connection with a ten port valve which has five pairs of ports in fluid communication internal to the valve in the OFF position where the pairs of ports in fluid communication are separated from each other by pairs of ports not in fluid communication internal to the valve when the valve is in the OFF position. When that ten port valve is in the ON position four of the five port pairs not in fluid communication internal to the valve when the valve is in the OFF position are in fluid communication internal to the valve and the present invention which is internal to the valve blocks the fifth such port pair from fluid communication.

As was described above such internal blocking conserves carrier gas when the ten port valve is in the ON position. It should be appreciated that using the present invention to internally block one or more port pairs when the valve is in one of its two operating modes may have applications beyond the conserving of carrier gas and can be used in ant valve that has at least four total ports.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A valve having at least four ports and first and second operating modes wherein when said valve is in said first operating mode said at least four ports become at least two pairs of adjacent ports in fluid communication with each other internal to said valve and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

a. first plate having on the periphery thereof said at least four ports for entry and exit of a first fluid, said at least four ports in fluid communication with at least four openings in each of first and second exterior surfaces of said first plate, each of said at least four openings associated with a respective one of said at least four ports, said at least four openings in said first exterior surface blocked when said valve is in said second operating mode;

b. a second plate having a valve for entry of a second fluid and a first exterior surface having at least one opening which is in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and a third plate having a valve for entry of said second fluid and a first exterior surface having at least two openings each of which are in fluid communication with said third plate second fluid entry valve, said third plate first exterior surface facing said first plate first exterior surface.

2. The multiport valve of claim 1 further comprising a second diaphragm between said first exterior surface of said first plate and said first exterior surface of said third plate, said second diaphragm pressing against said third plate first exterior surface when said valve is in said first operating mode.

3. The multiport valve of claim 2 wherein said second diaphragm presses against said first plate first exterior surface when said valve is in said second operating mode to thereby block said at least four openings in said first plate first exterior surface.

4. The multiport valve of claim 3 wherein flow of said second fluid in said third plate when said valve is in said second operating mode causes said second diaphragm to block said at least four openings in said first plate first exterior surface.

5. A valve having at least four ports and first and second operating modes wherein when said valve is in said first operating mode said at least four ports become at least two pairs of adjacent ports in fluid communication with each other internal to said valve and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

a. first plate having on the periphery thereof said at least four ports for entry and exit of a first fluid, said at least four ports in fluid communication with at least four openings in each of first and second exterior surfaces of said first plate, each of said at least four openings associated with a respective one of said at least four ports, said at least four openings in said first exterior surface blocked when said valve is in said second operating mode;

b. a second plate having a valve for entry of a second fluid and a first exterior surface having at least one opening which is in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and wherein flow of said second fluid in said second plate when said valve is in said first operating mode causes said first diaphragm to block said at least four openings in said first plate second exterior surface.

6. A valve having at least four ports and first and second operating modes wherein when said valve is in said first operating mode said at least four ports become at least two pairs of adjacent ports in fluid communication with each other internal to said valve and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

a. first plate having on the periphery thereof said at least four ports for entry and exit of a first fluid, said at least four ports in fluid communication with at least four openings in each of first and second exterior surfaces of said first plate, each of said at least four openings associated with a respective one of said at least four ports, said at least four openings in said first exterior surface blocked when said valve is in said second operating mode;

b. a second plate having a valve for entry of a second fluid and a first exterior surface having at least one opening which is in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and a second diaphragm which presses against said first plate first exterior surface when said valve is in said second operating mode to thereby block said at least four openings in said first plate exterior surface.

7. A process gas chromatograph comprising:

a. a multiport valve;

b. at least one separation column connected to a port of said multiport valve;

c. at least one detector connected to said at least one separation column;

said multiport valve having at least four ports and first and second operating modes wherein when said valve is in said first operating mode said at least four ports become at least two pairs of adjacent ports in fluid communication with each other internal to said and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

i. a first plate having on the periphery thereof said at least four ports for entry and exit of a first fluid, said at least four ports in fluid communication with at least four openings on each of first and second exterior surfaces of said first plate each of said at least four openings associated with a respective one of said at least four ports, said at least four openings on said first exterior surface blocked when said valve is in said second operating mode;

ii. a second plate having a valve for entry of a second fluid and a first exterior surface having at least one opening which is in fluid communication with said second plate second fluid entry valve;

iii. A first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and wherein said multiport valve further comprises a third plate having a valve for entry of said second fluid and a first exterior surface having at least two openings each of which are in fluid communication with said third plate second fluid entry valve, said third plate first exterior surface facing said first plate first exterior surface.

8. The process gas chromatograph of claim 7 wherein said multiport valve further comprises a second diaphragm between said first exterior surface of said first plate and said first exterior surface of said third plate, said second diaphragm pressing against said third plate first exterior surface when said valve is in said first operating mode.

9. The process gas chromatograph of claim 8 wherein said multiport valve second diaphragm presses against said first plate first exterior surface when said valve is in said second operating mode to thereby block said at least four openings in said first plate first exterior surface.

10. The process gas chromatograph of claim 9 wherein flow of said second fluid in said multiport valve third plate when said valve is in said second operating mode causes said second diaphragm to block said at least four openings in said first plate first exterior surface.

11. A process gas chromatograph comprising:
a. a multiport valve;
b. at least one separation column connected to a port of said multiport valve;
c. at least one detector connected to said at least one separation column;
said multiport valve having at least four ports and first and second operating modes wherein when said valve is in said first operating mode said at least four ports become at least two pairs of adjacent ports in fluid communication with each other internal to said and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

i. a first plate having on the periphery thereof said at least four ports for entry and exit of a first fluid, said at least four ports in fluid communication with at least four openings on each of first and second exterior surfaces of said first plate each of said at least four openings associated with a respective one of said at least four ports, said at least four openings on said first exterior surface blocked when said valve is in said second operating mode;

ii. a second plate having a valve for entry of a second fluid and a first exterior surface having at least one opening which is in fluid communication with said second plate second fluid entry valve;

iii. A first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and wherein flow of said second fluid in said multiport valve second plate when said valve is in said first operating mode causes said first diaphragm to block said at least four openings in said first plate second exterior surface.

12. A process gas chromatograph comprising:
a. a multiport valve;
b. at least one separation column connected to a port of said multiport valve;
c. at least one detector connected to said at least one separation column;
said multiport valve having at least four ports and first and second operating modes wherein when said valve is in said first operating mode said at least four ports become at least two pairs of adjacent ports in fluid communication with each other internal to said and at least two pairs of adjacent ports not in fluid communication with each other internal to said valve, at least one pair of said at least two adjacent port pairs not in fluid communication with each other internal to said valve when said valve is in said first operating mode separating at least one pair of said at least two port pairs that are in fluid communication with each other internal to valve when said valve is in said first operating mode, said valve comprising:

i. a first plate having on the periphery thereof said at least four ports for entry and exit of a first fluid, said at least four ports in fluid communication with at least four openings on each of first and second exterior surfaces of said first plate each of said at least four openings associated with a respective one of said at least four ports, said at least four openings on said first exterior surface blocked when said valve is in said second operating mode;

ii. a second plate having a valve for entry of a second fluid and a first exterior surface having at least one opening which is in fluid communication with said second plate second fluid entry valve;

iii. A first diaphragm between said second exterior surface of said first plate and said first exterior surface of said second plate, said first diaphragm pressing against said second plate first exterior surface when said valve is in said second operating mode;

said at least one opening in said first exterior surface of said second plate allowing when said valve is in said second operating mode fluid communication internal to said valve between all but at least one of said at least two port pairs not in fluid communication with each other internal to said valve when said valve is in said first operating mode; and wherein said multiport valve further comprises a second diaphragm which presses against said first plate first exterior surface when said valve is in said second operating mode to thereby block said at least four openings in said first plate exterior surface.

13. A valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with each other internal to valve when said valve is in said first operating mode, said valve comprising:

a. a first plate having on the periphery thereof said at least 2N ports for entry and exit of a first fluid, said at least 2N ports in fluid communication with at least 2N openings in each of first and second exterior surfaces of said first plate, each of said at least 2N openings associated with a respective one of said at least 2N ports, said at least 2N openings in said first exterior surface blocked when said valve is in said second operating mode;

b. a second plate having a valve for entry of a second fluid and a first exterior surface having at least N-1 openings each of which are in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least N-1 openings in said first exterior surface of said second plate allowing when said valve is in said second operating mode fluid communication internal to said valve between all but at least one of said at least N port pairs not in fluid communication with each other internal to said valve when said valve is in said first operating mode; and a third plate having a valve for entry of said second fluid and a first exterior surface having at least N openings each of which are in fluid communication with said third plate second fluid entry valve, said third plate first exterior surface facing said first plate first exterior surface.

14. The multiport valve of claim 13 further comprising a second diaphragm between said first exterior surface of said first plate and said first exterior surface of said third plate, said second diaphragm pressing against said third plate first exterior surface when said valve is in said first operating mode.

15. The multiport valve of claim 14 wherein said second diaphragm presses against said first plate first exterior surface when said valve is in said second operating mode to thereby block said at least 2N openings in said first plate first exterior surface.

16. The multiport valve of claim 15 wherein flow of said second fluid in said third plate when said valve is in said second operating mode causes said second diaphragm to block said at least 2N openings in said first plate first exterior surface.

17. A valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with each other internal to valve when said valve is in said first operating mode, said valve comprising:

a. a first plate having on the periphery thereof said at least 2N ports for entry and exit of a first fluid, said at least 2N ports in fluid communication with at least 2N openings in each of first and second exterior surfaces of said first plate, each of said at least 2N openings associated with a respective one of said at least 2N ports, said at least 2N openings in said first exterior surface blocked when said valve is in said second operating mode;

b. a second plate having a valve for entry of a second fluid and a first exterior surface having at least N-1 openings each of which are in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least N-1 openings in said first exterior surface of said second plate allowing when said valve is in said second operating mode fluid communication internal to said valve between all but at least one of said at least N port pairs not in fluid communication with each other internal to said valve when said valve is in said first operating mode; and wherein flow of said second fluid in said second plate when said valve is in said first operating mode causes said first diaphragm to block said at least 2N openings in said first plate second exterior surface.

18. A valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with each other internal to valve when said, valve is in said first operating mode, said valve comprising:

a. a first plate having on the periphery thereof said at least 2N ports for entry and exit of a first fluid, said at least 2N ports in fluid communication with at least 2N openings in each of first and second exterior surfaces of said first plate, each of said at least 2N openings associated with a respective one of said at least 2N ports, said at least 2N openings in said first exterior surface blocked when said valve is in said second operating mode;

b. a second plate having a valve for entry of a second fluid and a first exterior surface having at least N−1 openings each of which are in fluid communication with said second plate second fluid entry valve;

c. a first diaphragm between said second exterior surface of said first plate and said first exterior surface of said second plate, said first diaphragm pressing against said second plate first exterior surface when said valve is in said second operating mode;

said at least N−1 openings in said first exterior surface of said second plate allowing when said valve is in said second operating mode fluid communication internal to said valve between all but at least one of said at least N port pairs not in fluid communication with each other internal to said valve when said valve is in said first operating mode; and a second diaphragm which presses against said first plate first exterior surface when said valve is in said second operating mode to thereby block said at least 2N openings in said first plate exterior surface.

19. A process gas chromatograph comprising:
a. a multiport valve;
b. at least one separation column connected to a port of said multiport valve;
c. at least one detector connected to said at least one separation column;
said multiport valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with,each other internal to valve when said valve is in said first operating mode, said valve comprising;

i. a first plate having on the periphery thereof said at least 2N ports for entry and exit of a first fluid, said at least 2N ports in fluid communication with at least four openings on each of first and second exterior surfaces of said first plate each of said at least 2N openings associated with a respective one of said at least 2N ports, said at least 2N openings on said first exterior surface blocked when said valve is in said second operating mode;

ii. a second plate having a valve for entry of a second fluid and a first exterior surface having at least N−1 openings which are in fluid communication with said second plate second fluid entry valve;

iii. a first diaphragm between said second exterior surface of said first plate and said first exterior surface of said second plate, said first diaphragm pressing against said second plate first exterior surface when said valve is in said second operating mode;

said at least N−1 openings in said first exterior surface of said second plate allowing when said valve is in said second operating mode fluid communication internal to said valve between all but at least one of said at least N port pairs not in fluid communication with each other internal to said valve when said valve is in said first operating mode; and wherein said multiport valve further comprises a third plate having a valve for entry of said second fluid and a first exterior surface having at least N openings each of which are in fluid communication with said third plate second fluid entry valve, said third plate first exterior surface facing said first plate first exterior surface.

20. The process gas chromatograph of claim 19 wherein said multiport valve further comprises a second diaphragm between said first exterior surface of said first plate and said first exterior surface of said third plate, said second diaphragm pressing against said third plate first exterior surface when said valve is in said first operating mode.

21. The process gas chromatograph of claim 20 wherein said multiport valve second diaphragm presses against said first plate first exterior surface when said valve is in said second operating mode to thereby block said at least 2N openings in said first plate first exterior surface.

22. The process gas chromatograph of claim 21 wherein flow of said second fluid in said multiport valve third plate when said valve is in said second operating mode causes said second diaphragm to block said at least 2N openings in said first plate first exterior surface.

23. A process gas chromatograph comprising:
a. multiport valve;
b. at least one separation column connected to a port of said multiport valve;
c. at least one detector connected to said at least one separation column;
said multiport valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with each other internal to valve when said valve is in said first operating mode, said valve comprising;

i. a first plate having on the periphery thereof said at least 2N ports for entry and exit of a first fluid, said at least 2N ports in fluid communication with at least four openings on each of first and second exterior surfaces of said first plate each of said at least 2N openings associated with a respective one of said at least 2N ports, said at least 2N openings on said first exterior surface blocked when said valve is in said second operating mode;

ii. a second plate having a valve for entry of a second fluid and a first exterior surface having at least N–1 openings which are in fluid communication with said second plate second fluid entry valve;

iii. a first diaphragm between said second exterior surface of said first plate and said first exterior surface of said second plate, said first diaphragm pressing against said second plate first exterior surface when said valve is in said second operating-mode;

said at least N–1 openings in said first exterior surface of said second plate allowing when said valve is in said second operating mode fluid communication internal to said valve between all but at least one of said at least N port pairs not in fluid communication with each other internal to said valve when said valve is in said first operating mode; and wherein flow of said second fluid in said multiport valve second plate when said valve is in said first operating mode causes said first diaphragm to block said at least 2N openings in said first plate second exterior surface.

24. A process gas chromatograph comprising:

a. a multiport valve;

b. at least one separation column connected to a port of said multiport valve;

c. at least one detector connected to said at least one separation column;

said multiport valve having at least 2N ports, where N≧2, and first and second operating modes wherein when said valve is in said first operating mode said at least 2N ports become at least N pairs of adjacent ports in fluid communication with each other internal to said valve and at least N pairs of adjacent ports not in fluid communication with each other internal to said valve, at least one pair of said at least N adjacent port pairs not in fluid communication with each other internal to said valve when said valve is in said first operating mode separating at least one pair of said at least N port pairs that are in fluid communication with each other internal to valve when said valve is in said first operating mode, said valve comprising;

i. a first plate having on the periphery thereof said at least 2N ports for entry and exit of a first fluid, said at least 2N ports in fluid communication with at least four openings on each of first and second exterior surfaces of said first plate each of said at least 2N openings associated with a respective one of said at least 2N ports, said at least 2N openings on said first exterior surface blocked when said valve is in said second operating mode;

ii. a second plate having a valve for entry of a second fluid and a first exterior surface having at least N–1 openings which are in fluid communication with said second plate second fluid entry valve;

iii. a first diaphragm between said second exterior surface of said first plate and said first exterior surface of said second plate, said first diaphragm pressing against said second plate first exterior surface when said valve is in said second operating-mode;

said at least N–1 openings in said first exterior surface of said second plate allowing when said valve is in said second operating mode fluid communication internal to said valve between all but at least one of said at least N port pairs not in fluid communication with each other internal to said valve when said valve is in said first operating mode; and wherein said multiport valve further comprises a second diaphragm which presses against said first plate first exterior surface when said valve is in said second operating mode to thereby block said at least four openings in said first plate exterior surface.

* * * * *